United States Patent
Mansfield et al.

(10) Patent No.: US 6,344,337 B1
(45) Date of Patent: Feb. 5, 2002

(54) ANTIGEN TEST TO DETECT EQUINE PROTOZOAL MYELOENCEPHALITIS IN HORSE SERUM AND CEREBROSPINAL FLUID

(75) Inventors: Linda S. Mansfield, Bath; Mary G. Rossano, Mason; Alice J. Murphy, St. Johns; Ruth A. Vrable, Williamston, all of MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 09/506,630

(22) Filed: Feb. 18, 2000

Related U.S. Application Data

(60) Provisional application No. 60/120,831, filed on Feb. 19, 1999, and provisional application No. 60/152,193, filed on Sep. 2, 1999.

(51) Int. Cl.$^7$ ................................................ G01N 33/53
(52) U.S. Cl. ........................ 435/7.2; 435/34; 530/388.6
(58) Field of Search .................... 435/7.1, 34; 530/388.6

(56) References Cited

U.S. PATENT DOCUMENTS

| | | |
|---|---|---|
| 4,486,530 A | 12/1984 | David et al. |
| 4,786,589 A | 11/1988 | Rounds et al. |
| 4,939,096 A | 7/1990 | Tonelli |
| 4,965,187 A | 10/1990 | Tonelli |
| 5,079,172 A | 1/1992 | Hari et al. |
| 5,166,078 A | 11/1992 | McMahon et al. |
| 5,169,789 A | 12/1992 | Bernstein et al. |
| 5,177,014 A | 1/1993 | O'Conner et al. |
| 5,219,725 A | 6/1993 | O'Conner et al. |
| 5,223,424 A | 6/1993 | Cochran et al. |
| 5,229,293 A | 7/1993 | Matsuura et al. |
| 5,256,372 A | 10/1993 | Brooks et al. |
| 5,338,683 A | 8/1994 | Paoletti et al. |
| 5,356,785 A | 10/1994 | McMahon et al. |
| 5,494,807 A | 2/1996 | Paoletti et al. |
| 5,518,892 A | 5/1996 | Naqui et al. |
| 5,559,041 A | 9/1996 | Kang et al. |
| 5,620,845 A | 4/1997 | Gould et al. |
| 5,620,895 A | 4/1997 | Naqui et al. |
| 5,627,026 A | 5/1997 | O'Conner et al. |
| 5,656,448 A | 8/1997 | Kang et al. |
| 5,695,928 A | 12/1997 | Stewart et al. |
| 5,700,655 A | 12/1997 | Croteau et al. |
| 5,726,010 A | 3/1998 | Clark |
| 5,726,013 A | 3/1998 | Clark |
| 5,728,587 A | 3/1998 | Kang et al. |
| 5,747,476 A | 5/1998 | Russell |
| 5,750,333 A | 5/1998 | Clark |
| 5,753,456 A | 5/1998 | Naqui et al. |
| 5,830,893 A | 11/1998 | Russell |
| 5,883,095 A | 3/1999 | Granstrom et al. |
| 5,925,622 A | 7/1999 | Rossignol et al. |
| 5,928,913 A | 7/1999 | Efstathiou et al. |
| 5,935,591 A | 8/1999 | Rossignol et al. |
| 5,935,777 A | 8/1999 | Moyer et al. |
| 5,976,896 A | 11/1999 | Kumar et al. |
| 5,977,322 A | 11/1999 | Marks et al. |
| 5,985,594 A | 11/1999 | Croteau et al. |

OTHER PUBLICATIONS

McKay et al., The Compendium of Continuing Education for Practicing Veterinarians 14: 1359–1366 (1997).
Blythe et al., J. Am. Vet. Med. Assoc. 210: 525–527 (1997).
Saville et al., J. Am. Vet. Assoc. 210: 519–524 (1997).
Bentz et al., J. Am. Vet Med. Assoc. 210: 517–518 (1997).
Granstom et al., J. Vet. Diag. Invest. 5: 88–90 (1993).
Fenger et al., Vet Parasitol. 68: 199–213 (1997).
Martenuik et al., The Conference of Research Workers in Animal Diseases, Nov. 10–11, Chicago, IL (1997).
Engvall et al., Immunochem. 8: 871 (1971).
Ljunggren et al., J. Immunol. Meth. 88: 104 (1987).
Kemeny et al., Immunol. Today 7: 67 (1986).
Antibodies, A Laboratory Manual, eds. Harlow and Lane, Cold Spring Harbor Laboratory Press, Cold Spring Harbor, New York (1988).
Fenger et al., J. Parasitol. 81: 199–213 (1995).
Molecular Cloning: A Laboratory Manual, Second Edition, edited by Sambrook et al. Cold Spring Harbor Lab. Press, Cold Spring Harbor, New York (1989).
In Current Protocols in Molecular Biology, section 3.8 (vol. 1) (1988).
Sloss et al., In Veterinary Clinical Parasitology, Iowa State Univ.Press, Ames, Iowa (1994) p. 198.
Marsh et al., J. Parasitology 83: 1189–1192 (1997).
Speer et al., J. Protozoology 33: 486–490 (1986).
Liang, F. T.; Granstrom D.E.; Zhao, X.M.; and Timoney, J.F.; "Evidence that Sur. Pro . . . " Infec. and Imm., May 1998, v. 66, No. 5, pp. 1834–1838.

*Primary Examiner*—Hankyel T. Park
(74) *Attorney, Agent, or Firm*—Ian C. McLeod

(57) ABSTRACT

The present invention provides an immunoassay to detect identifying antigens in horses that are infected with *Sarcocystis neurona*. The immunoassay is preferably an antigen-capture-based assay that relies upon polyclonal or monoclonal antibodies against a 16 (±4) and/or 30 (±4) kDa antigens specific to Sarcocystis neurona to detect the presence of the 16 (±4) and/or 30 (±4) kDa antigens in equine serum or equine cerebrospinal fluid.

36 Claims, No Drawings

SEQUENCE LISTING

```
<160> NUMBER OF SEQ ID NOS: 3

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: reverse
      primer to Sarcocystis neurona SSURNA gene

<400> SEQUENCE: 1
ccattccgga cgcgggt                                                17

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: eukaryote
      universal forward primer

<400> SEQUENCE: 2
cgtggtgcat ggccg                                                  15

<210> SEQ ID NO 3
<211> LENGTH: 18
<212> TYPE: DNA
<213> ORGANISM: Artificial Sequence
<220> FEATURE:
```

-continued

```
<223> OTHER INFORMATION: Description of Artificial Sequence: reverse
      primer to the protist SSURNA gene

<400> SEQUENCE: 3
gcgcgtgcag cccagaac                                                   18
```

ANTIGEN TEST TO DETECT EQUINE PROTOZOAL MYELOENCEPHALITIS IN HORSE SERUM AND CEREBROSPINAL FLUID

CROSS-REFERENCE TO RELATED APPLICATION

The application claims the benefit of U.S. Provisional patent application Ser. No. 60/120,831, filed on Feb. 19, 1999 and Provisional patent application Ser. No. 60/152, 193, filed on Sep. 2, 1999.

STATEMENT REGARDING FEDERALLY SPONSORED RESEARCH OR DEVELOPMENT

None.

BACKGROUND OF THE INVENTION (1) Field of the Invention

The present invention relates to an immunoassay to detect identifying antigens in horses that are infected with *Sarcocystis neurona*. The immunoassay is preferably an antigen-capture-based assay that relies upon polyclonal or monoclonal antibodies against the 16 (±4) and/or 30 (±4) kDa antigens specific to *Sarcocystis neurona* to detect the presence of the 16 (±4) and/or 30 (±4) kDa antigens in equine serum or equine cerebrospinal fluid. The present invention further relates to polyclonal and monoclonal antibodies against the 16 (±4) and/or 30 (±4) kDa antigens, and DNA and clones encoding the 16 (±4) and/or 30 (±4) kDa antigens.

(2) Description of Related Art

Equine protozoal myeloencephalitis (EPM) is a neurological disease caused by the protozoan parasite *Sarcocystis neuronaa*. In recent years, EPM has caused significant health, economic, and emotional costs to horses and their owners (reviewed by McKay et al., The Compendium of Continuing Education for Practicing Veterinarians 14: 1359–1366 (1997). Opossums have been implicated as the natural reservoir of *Sarcocystis neurona* because the sexual stages of the parasite occur in the intestines of the opossum and the sporocysts are passed in the feces of the opossum. Horses accidentally eat the opossum feces containing the sporocysts when they are grazing; however, because *Sarcocystis neurona* does not appear to form mature tissue cysts in equines, equines are considered to be dead end hosts. Because opossums are ubiquitous in the United States, large numbers of horses are exposed to this parasite: approximately 50 to 60% of the horses nationwide (Blythe et al., J. Am. Vet. Med. Assoc. 210: 525–527 (1997), Saville et al., J. Am. Vet. Assoc. 210: 519–524 (1997), Bentz et al., J. Am. Vet. Med. Assoc. 210: 517–518 (1997)).

Currently, there are no in-field or horse-side diagnostic tests for determining whether a horse is currently infected with *Sarcocystis neuronaa*. A Western blot test was developed to detect antibodies to *Sarcocystis neurona* in cerebrospinal fluid of horses suspected of having EPM; however, these Western blot assays have not been reliable in predicting the presence of *Sarcocystis neurona* due to the prevalence in horses of cross-reacting antibodies to other Sarcocystis species (Granstom et al. J. Vet. Diag. Invest. 5: 88–90 (1993), Fenger et al., Vet. Parasitol. 68: 199–213 (1997), Bentz et al., ibid., Saville et al., ibid., Blythe et al., ibid.). More recently, an improved western blot diagnostic test was disclosed in U.S. application Ser. No. 09/156,954 which reliably measures the prevalence of antibodies against *Sarcocystis neurona* in horse serum or cerebrospinal fluid. The improved method measures the presence of identifying 16 (±4) and 30 (±4) kDa *Sarcocystis neurona* antigens on Western blots that have been pretreated with antibodies against bovine *Sarcocystis cruzi* which prevents binding to the western blot of antibodies that may be present in the horse serum against Sarcocystis spp. other than *Sarcocystis neuronaa*.

Currently, there are no vaccines to protect horses from the parasite, and current treatment regimens are effective in only about 50% of the horses (Martenuik et al., The Conference of Research Workers in Animal Diseases, Nov. 10–11, Chicago, Ill. (1997)). However, these studies on treatment efficacy were based on a low number of horses. The U.S. Department of Agriculture (USDA), Animal and Plant Health Inspection Service (APHIS), National Animal Health Monitoring System (NAHMS) of the Needs Assessment Survey (NAS) has designated EPM as one of the top two infectious diseases of national importance to the horse industry. Among veterinarians and race horse owners, EPM has been ranked as the leading health care concern. In particular, 58% of the race horse owners ranked EPM as the top health care concern.

Since there are no commercially available vaccines for EPM and EPM is a significant health concern of the equine industry, considerable effort has been directed towards developing therapeutic methods for treating EPM. For example, U.S. Pat. No. 5,935,591 to Rossignol et al. describes using thiazolides as a treatment for EPM; U.S. Pat. No. 5,883,095 to Granstrom et al. describes using triazine-based anti-coccidials as a treatment for EPM; U.S. Pat. No. 5,830,893 to Russel describes using triazinediones as a treatment for EPM; U.S. Pat. No. 5,747,476 to Russel describes using a combination of pyrimethamine and a sulfonamide, preferably sulfadiazine in the absence of known therapeutic amounts of trimethoprim as a treatment for EPM; and U.S. Pat. No. 5,925,622 to Rossignol et al. describes using aryl glucuronide of 2-hydroxy-N-(5-nitro-2-thiazolyl) benzamide as a treatment for EPM.

Treatment for EPM is expensive and cumbersome because of the long duration required to achieve positive results. Because many horses cannot be successfully treated, economically and emotionally valuable animals have been lost to EPM. However, the extent of EPM's economic impact is even greater because of the large sums of money spent by horse owners for treating lame horses which have been incorrectly diagnosed with EPM, for giving prophylactic treatments that have no scientific basis, and for finding positive post-race drug test results.

EPM has been the cause of hysteria in the equine industry. The small amount of scientific data available on EPM supports a high exposure rate of horses, but there are no data available that document the rate of clinical disease resulting from exposure to the parasite. Because of this, horse owners and veterinarians assume that the rate of clinical disease is high. As a result, several alarming consequences have arisen. Horses with lameness or other neurological diseases are being misdiagnosed as having EPM. People whose livelihoods depend on horses are resorting to medicating all their horses all of the time with antimicrobials. This approach to treating EPM is very widespread in the racing industry. However, this indiscriminate use of antimicrobials has the potential of leading to resistant bacteria such as Salmonella, *E. coli*, etc. which will then enter the environment and pose a risk for humans and animals. Thus, the repercussions of EPM may extend beyond a disease that merely affects the horse industry. All of the repercussions of EPM are expensive, decrease the value realized to the U.S. equine industry, and raise the specter of a public health problem of immense proportions.

For the above reasons, there is a need for a reliable diagnostic assay that can detect those horses that are infected with *Sarcocystis neurona*.

SUMMARY OF THE INVENTION

The present invention provides a method for detecting the presence of *Sarcocystis neurona* in an equine in an immunoassay, the improvement which comprises reacting a biological sample from the equine suspected of harboring the *Sarcocystis neurona* with an antibody against a *Sarcocystis neurona* antigen to form an antibody-antigen complex. In particular, the antigen is a *Sarcocystis neurona* specific antigen about 16 (±4) kDa and about 30 (±4) kDa. Optionally, the method provides a positive control consisting of the 16 (±4) and/or 30 (±4) kDa antigens or portion thereof.

In a preferred embodiment of the method a labeled antibody against the antigen or the antibody in the antibody-antigen complex is provided to the reaction for the detecting. Preferably, the label is selected from the group consisting of alkaline phosphatase, horseradish peroxidase, fluorescent compounds, luminescent compounds, colloidal gold, and magnetic particles. In a preferred embodiment, the label is biotin which is reacted with peroxidase conjugate and then detected by reaction with an appropriate color forming substrate.

Preferably, the biological sample is selected from the group consisting of serum, cerebrospinal fluid, and cell culture fluid from equine dermal cells infected with *Sarcocystis neurona* from a biological sample. In a preferred embodiment, the antibody against the antigen is immobilized on a support selected from the group consisting of a membrane or a plate.

The present invention also provides a method for detecting the presence of *Sarcocystis neurona* in an equine in an immunoassay, the improvement which comprises reacting a biological sample from the equine suspected of harboring the *Sarcocystis neurona* with a monoclonal antibody against a *Sarcocystis neurona* antigen to form an antibody-antigen complex. In particular, the present invention relates to an immunoassay wherein the antigen is a *Sarcocystis neurona* specific antigen about 16 (±4) kDa and/or about 30 (±4) kDa.

In a preferred embodiment, a labeled antibody against the antigen or the antibody in the monoclonal antibody-antigen complex is provided to the reaction for the detecting. In particular, wherein the label is selected from the group consisting of alkaline phosphatase, horseradish peroxidase, fluorescent compounds, luminescent compounds, colloidal gold, and magnetic particles. In a preferred embodiment, the label is biotin which is reacted with peroxidase conjugate and then detected by reaction with an appropriate color forming substrate.

It is preferable that the biological sample is selected from the group consisting of serum, cerebrospinal fluid, and cell culture fluid from equine dermal cells infected with *Sarcocystis neurona* from a biological sample. The present invention further provides for the immunoassay wherein the monoclonal antibody against the antigen is immobilized on a support selected from the group consisting of a membrane or a plate. In a preferred embodiment of the present invention, the labeled antibody is a second monoclonal antibody.

The present invention further provides a method for detecting *Sarcocystis neurona* in an immunoassay comprising: (a) reacting a biological sample from an equine suspected of harboring the *Sarcocystis neurona* with a monoclonal antibody to an antigen of the *Sarcocystis neurona* which is immobilized on a support wherein the monoclonal antibody forms a complex with the antigen, and (b) detecting the complex. In particular, wherein the antigen is about 16 kDa (±4) or 30 (±4) kDa. Optionally, the method provides a positive control consisting of the 16 (±4) and/or 30 (±4) kDa antigens or portion thereof.

In a preferred embodiment, the complex is detected by a labeled antibody against the antigen or monoclonal antibody in the complex. Particularly, wherein the labeled antibody is a second monoclonal antibody. In the method, the label is selected from the group consisting of alkaline phosphatase, horseradish peroxidase, fluorescent compounds, luminescent compounds, colloidal gold, and magnetic particles. Preferably, the label is biotin which is reacted with peroxidase conjugate and then detected by reaction with an appropriate color forming substrate.

In the method, it is desirable that the biological sample is selected from the group consisting of serum, cerebrospinal fluid, and cell culture fluid from equine dermal cells infected with *Sarcocystis neurona* from a biological sample. In a preferred embodiment, the monoclonal antibody against the antigen is immobilized on a support selected from the group consisting of a membrane or a plate.

The present invention also provides a kit for detecting *Sarcocystis neurona* in a biological sample from an equine comprising: (a) one or more monoclonal or polyclonal antibodies to one or more identifying antigens of *Sarcocystis neurona* to form a complex; (b) a positive control comprising one or more identifying antigens of *Sarcocystis neuronaa*; and (c) a reagent for detection of the complex formed between the monoclonal antibody and the antigen of *Sarcocystis neuronaa*. In particular, wherein the antigens are 16 (±4) and/or 30 (±4) kDa.

In a preferred embodiment, the reagent for detecting the complex consists of a labeled antibody against the antigen or antibody in the complex. In the kit, the label is selected from the group consisting of alkaline phosphatase, horseradish peroxidase, fluorescent compounds, luminescent compounds, colloidal gold, and magnetic particles. Preferably, the label is biotin which is reacted with peroxidase conjugate and then detected by reaction with an appropriate color forming substrate.

In the kit, the biological sample is from the group consisting of serum, cerebrospinal fluid, and cell culture fluid from equine dermal cells infected with *Sarcocystis neurona* from a biological sample. In a preferred embodiment of the kit, the monoclonal antibody against the antigen is immobilized on a support selected from the group consisting of a membrane or a plate. Further, it is preferable that the labeled antibody is a second monoclonal antibody or specific polyclonal antibody.

Finally, the present invention provides a kit for the detection of evidence of disease caused by *Sarcocystis neurona* in equines which comprises: (a) a support with at least one monoclonal antibody against a first epitope of one or more identifying antigens of the *Sarcocystis neurona* immobilized on a surface of the support to bind the identifying antigens in a biological sample; (b) a labeled monoclonal antibody against a second epitope of one or more of the identifying antigens to bind the identifying antigens in a biological sample; and (c) at least one reagent for detection of the labeled monoclonal antibody.

In the kit, it is preferable that the label is selected from the group consisting of alkaline phosphatase, horseradish peroxidase, fluorescent compounds, luminescent compounds, colloidal gold, and magnetic particles. In particular, wherein the label is biotin which is reacted with peroxidase conjugate and then detected by reaction with an appropriate color forming substrate.

It is preferred that the biological sample is selected from the group consisting of serum, cerebrospinal fluid, and cell culture fluid from equine dermal cells infected with *Sarcocystis neurona* from a biological sample. In a preferred embodiment, the monoclonal antibody against the antigen is immobilized on a support selected from the group consisting of a membrane or a plate.

The present invention also provides a monoclonal antibody against a 16 (±4) kDa antigen of *Sarcocystis neuronaa*, a monoclonal antibody against a 30 (±4) kDa antigen of *Sarcocystis neuronaa*, an isolated DNA encoding a 16 (±4) kDa antigen of *Sarcocystis neuronaa*, and an isolated DNA encoding a 30 (±4) kDa antigen of *Sarcocystis neurona*.

OBJECTS

It is therefore an object of the present invention to provide an immunoassay method and test kit to detect the presence of *Sarcocystis neurona* antigens in a biological sample of an equine which are a result of infection by *Sarcocystis neuronaa*, the causative agent of protozoal myeloencephalitis in equines. In particular, it is an object of the present invention to provide a method that is relatively easy to perform, and is accurate and economical.

These and other objects of the present invention will become increasingly apparent by reference to the following embodiments and drawings.

DESCRIPTION OF PREFERRED EMBODIMENTS

The following definitions are provided herein to promote a better understanding of the present invention.

The term "antibody" as used herein refers to an immunoglobulin molecule with the capacity to bind with a specific antigen as the result of a specific immune response. Immunoglobulins are serum proteins made up of light and heavy polypeptide chains and divisible into classes, which contain within them antibody activities toward a wide range of antigens.

The term "polyclonal antibody" as used herein refers to a mixed population of antibodies made against a particular pathogen or antigen. In general, the population contains a variety of antibody groups, each group directed towards a particular epitope of the pathogen or antigen. To make polyclonal antibodies, the whole pathogen or an isolated antigen is introduced by inoculation or infection into a host which induces the host to make antibodies against the pathogen or antigen.

The term "monoclonal antibody" as used herein refers to antibodies produced by a single line of hybridoma cells all directed towards one epitope on a particular antigen. The antigen used to make the monoclonal antibody can be provided as an isolated protein of the pathogen or the whole pathogen. A hybridoma is a clonal cell line that consists of hybrid cells formed by the fusion of a myeloma cell and a specific antibody-forming cell. In general, monoclonal antibodies are of mouse origin; however, monoclonal antibody also refers to a clonal population of an antibody made against a particular epitope of an antigen produced by phage display technology or method that is equivalent to phage display or hybrid cells of non-mouse origin.

The term "antigen" as used herein refers to a substance which stimulates production of antibody or sensitized cells during an immune response. An antigen includes the whole pathogen or a particular protein or polypeptide of the pathogen. An antigen consists of multiple epitopes, each epitope of which is capable of causing the production of an antibody against the particular epitope. Thus, as used herein antigen also refers to a particular epitope of the protein or polypeptide.

The term "epitope" as used herein refers to an immunogenic region of an antigen which is recognized by a particular antibody molecule. In general, an antigen will possess one or more epitopes, each capable of binding an antibody that recognizes the particular epitope. An antibody can recognize a contiguous epitope which is an epitope that is a linear sequence of amino acids in the antigen molecule, or a non-contiguous epitope which is an epitope that spans non-contiguous amino acids in the antigen which are brought together as a result of the three-dimensional structure of the antigen.

The term "immunoassay" as used herein refers to an analytical method which uses the ability of an antibody to bind a particular antigen as the means for determining the presence of the antigen. An antibody-capture immunoassay is an assay that provides an antigen which is used to detect antibodies against a particular pathogen in a biological sample of a test subject. In general, the antigen is immobilized on a support and is capable of binding an antibody in a biological sample. An antigen-capture assay is an assay that provides an antibody against a particular pathogen which is used to detect a particular antigen in a biological sample from a test subject. In general, the antibody, which can be a monoclonal or polyclonal antibody, is immobilized on a support. The antigen is provided by the biological sample. In a variation of the antigen-capture assay the antibody is mixed with the antigen in the biological sample and the antigen-antibody complex thus formed is captured by a second antibody against the antigen or antibody or both in the antigen-antibody complex which is immobilized on a support. Alternatively, the formation of the antigen-antibody complex is measured in solution.

The term "immunodiffusion" as used herein refers to a method wherein a biological sample is applied to support and allowed to diffuse throughout the support wherein an antigen in the sample binds to an antibody against the antigen which is immobilized to a particular region of the support.

The term "seroconversion" as used herein refers to the appearance of antibodies to a pathogen in animals not normally exposed to the pathogen. Seroconversion is used as a measure of potential spread of a particular disease in previously unexposed populations.

The present invention provides an antigen-capture immunoassay for determining whether an equine is infected with *Sarcocystis neuronaa*. In the preferred embodiment, the assay uses a monoclonal antibody against an epitope of a 16 (±4) and/or 30 (±4) kDa antigen to detect the corresponding antigen in a biological sample from an equine. Preferably, the biological sample is a serum or cerebrospinal fluid sample from an equine.

In U.S. Ser. No. 09/156,954, filed on Sep. 18, 1998, which is hereby incorporated herein by reference, disclosing a Western blot assay, it was found that antibodies against the antigens of other Sarcocystis sp. will cross-react with the immunodominant antigens of *Sarcocystis neuronaa*. Because these antibodies against other Sarcocystis sp. cross-react with *Sarcocystis neurona* antigens, testing a biological sample from an equine that had been exposed to another Sarcocystis sp., but not Sarcocystis neurona, would produce a result that falsely indicated that the equine had been exposed to *Sarcocystis neuronaa*. The false-positive results made it difficult to determine whether an equine had been exposed to *Sarcocystis neuronaa*. Therefore, U.S. Ser. No. 09/156,954 disclosed an improved immunoassay that reduced the risk of false-positives. It was discovered that *Sarcocystis neurona* possessed two identifying antigens, a 16 (±4) antigen and a 30 (±4) kDa antigen, which did not cross-react with antibodies from other Sarcocystis spp. Thus, a Western blot immunoassay was developed which comprised reacting serum or cerebrospinal fluid from an equine with the total proteins of *Sarcocystis neurona* that had been resolved by gel electrophoresis and immobilized on a support. To prevent non-specific binding of antibodies against other Sarcocystis spp. which could be present in the serum to the *Sarcocystis neurona* proteins immobilized on the support, the Western blot was first reacted with bovine antibodies against a Sarcocystis sp. other than *Sarcocystis neuronaa*. Since other Sarcocystis spp. do not make antibodies against the identifying antigens of *Sarcocystis neuronaa*, only equine samples that contained antibodies against the identifying antigens would bind the identifying antigens and, thus, be detectable when the Western blot was developed with labeled anti-horse IgG antibodies.

By identifying the antigens that were specific for *Sarcocystis neuronaa*, the immunoassay of U.S. Ser. No. 09/156,954 improved the specificity of immunoassays for detecting *Sarcocystis neurona* antibodies in serum; however, these immunoassays are limited to only indicating that an equine had been exposed to *Sarcocystis neurona* at some time in its life. These immunoassays can not distinguish between (1) an equine that had been exposed to *Sarcocystis neurona* but was not actively infected from (2) an equine that was actively infected with *Sarcocystis neuronaa*. Nor can the immunoassays distinguish between an equine that had been vaccinated against *Sarcocystis neurona* from an equine that had not been vaccinated. Furthermore, the immunoassays are dependent on seroconversion of the equine and could not detect equine that were infected but had not or could not seroconvert. Also, because the immunoassays detect antibodies, and antibodies persist for a period of time after infection, the immunoassay can not distinguish between an equine that has been successfully treated for EPM from an equine in which the treatment failed.

For the above reasons, the antigen-capture immunoassay of the present invention is an improvement in detecting equine infected with *Sarcocystis neuronaa*. The immunoassay of the present invention enables the diagnosis of EPM to be made with high accuracy and specificity. In contrast to antibody-capture immunoassays, the antigen-capture immunoassay of the present invention enables equines that are actively infected with *Sarcocystis neurona* to be distinguished from equines that had been infected with *Sarcocystis neurona* but are either no longer infected or have not mounted an effective immune response. Thus, a major limitation of antibody-capture assays is avoided. Furthermore, the present invention can distinguish between equines that have been vaccinated and are producing antibodies against the vaccine from equines that have not been vaccinated but are or have been infected with *Sarcocystis neuronaa*. For the aforementioned reasons, the antigen-capture immunoassay of the present invention reduces the risk of misdiagnosis and inappropriate treatments.

Thus, the present invention provides an antigen-capture immunoassay that detects *Sarcocystis neurona* antigens in a biological sample of an equine, preferably a serum or cerebrospinal fluid sample. In particular, the immunoassay detects the presence of the *Sarcocystis neurona* 16 (±4) and 30 (±4) kDa antigens in the biological sample. The present invention uses a monoclonal antibody or mixture of monoclonal antibodies against one or more epitopes of the 16 (±4) and/or 30 (±4) kDa antigens to detect whether the antigens are present in the biological sample. Monoclonal antibodies are preferred because they enable antigen-based immunoassays to be performed with a very high degree of specificity and sensitivity. Furthermore, because the monoclonal antibodies are highly specific for the 16 (±4) and 30 (±4) kDa antigens, the present invention does not need to rely on Western blots to identify the *Sarcocystis neurona* antigens. Therefore, both ELISA-based and immunodiffusion-based assays are within the scope of the present invention.

The antigen-capture immunoassay of the present invention is preferably a solid phase immunoassay or derivative thereof. An example of a solid phase immunoassay is an enzyme-linked immunosorbent assay (ELISA) developed by Engvall et al., *Immunochem.* 8: 871 (1971) and further refined by others such as Ljunggren et al. *J. Immunol. Meth.* 88: 104 (1987) and Kemeny et al., *Immunol. Today*7: 67 (1986). ELISA and its variations are well known in the art.

For example, in a preferred ELISA of the present invention, antigens in a biological sample from an equine suspected of being infected with *Sarcocystis neurona* form a complex with a monoclonal antibody to the antigens wherein the monoclonal antibody is immobilized on a surface prior to forming the monoclonal antibody-antigen complex. The monoclonal antibody or mixture of monoclonal antibodies is specific for one or more epitopes of the 16 (±4) and/or 30 (±4) kDa antigens. Thus, the monoclonal antibody is immobilized on a surface by methods well known in the art, preferably in the wells of a microtiter plate which is commonly used for ELISA assays. Next, the biological sample is added to the wells containing the bound monoclonal antibodies and the antigen in the biological sample is allowed to bind to the monoclonal antibodies. The biological sample can be provided neat or in a limiting dilution series in a physiological solution. Unbound material in the sample is removed from the immobilized antibody-antigen complex by washing. The complex is then reacted with a second monoclonal antibody that complexes with the antigen to form a second complex consisting of the monoclonal antibody-antigen-second monoclonal antibody. Alternatively, the second antibody can be a polyclonal antibody since it is unlikely that after washing there would be any Sarcocystis sp. antigens that could cross-react with *Sarcocystis neuronaa*-specific polyclonal antibodies. The second complex can be detected when the second monoclonal or polyclonal antibody is conjugated to a reporter ligand such as horseradish-peroxidase or alkaline phosphatase. Alternatively, the second monoclonal or polyclonal antibody can be conjugated to reporter ligands such as a fluorescing ligand, biotin, colored latex, colloidal gold magnetic beads, radioisotopes or the like. Detection of the complex is by methods well known in the art for detecting the particular reporter ligand. In some instances, it is desirable that the monoclonal or polyclonal antibody against the identifying antigens of *Sarcocystis neurona* is not conjugated to a reporter ligand. In that instance, a third antibody is provided which is conjugated to a reporter ligand and is against the type of antibody comprising the monoclonal or polyclonal antibody, e.g., in the case of the monoclonal antibody, the third antibody is against mouse antibodies.

A variation of the ELISA is disclosed in U.S. Pat. No. 5,079,172 to Hari et al. which is hereby incorporated herein by reference. While Hari et al. discloses spheres coated with antigen, one skilled in the art would recognize that the spheres could be coated with monoclonal antibodies against the 16 (±4) and/or 30 (±4) kDa antigens.

Other immunoassays that are suitable for performing the present invention are disclosed in U.S. Pat. No. 5,620,845 to Gould et al.; U.S. Pat. No. 4,486,530 to David et al.; U.S. Pat. No. 5,559,041 to Kang et al.; U.S. Pat. No. 5,656,448 to Kang et al.; U.S. Pat. No. 5,728,587 to Kang et al.; U.S. Pat. No. 5,695,928 to Stewart et al.; U.S. Pat. No. 5,169,789 to Bernstein et al.; U.S. Pat. Nos. 5,177,014, 5,219,725, and 5,627,026 to O'Conner et al.; U.S. pat. No. 5,976,896 to Kumar et al.; U.S. Pat. Nos. 4,939,096 and 4,965,187 to Tonelli; U.S. Pat. No. 5,256,372 to Brooks et al.; U.S. Pat. Nos. 5,166,078 and 5,356,785 to McMahon et al.; U.S. Pat. Nos. 5,726,010, 5,726,013, and 5,750,333 to Clark; U.S. Pat. Nos. 5,518,892, 5,753,456, and 5,620,895 to Naqui et al.; U.S. Pat. Nos. 5,700,655 and 5,985,594 to Croteau et al.; and U.S. Pat. No. 4,786,589 to Rounds et al. The aforementioned U.S. patents are hereby incorporated herein by reference. In all the aforementioned, the immunoassay is modified to detect the 16 (±4) and/or 30 (±4) kDa antigens in a biological sample of an equine, preferably the serum or cerebrospinal fluid.

The immunoassay of the present invention can also be provided as a kit. In one embodiment, the kit provides a microtiter plate or equivalent wherein a series of wells are coated with the monoclonal antibody. A second series of wells are coated with a non-reactive antigen such as bovine serum albumen. The second series of wells serves as a negative control. Optionally, a third series of wells coated with the purified 16 (±4) and/or 30 (±4) kDa antigens is provided. The third series of wells serves as a positive control for the detection method included with the kit. To test a biological sample, the sample is cleared of red blood cells, if present, by standard methods available in any medical laboratory. The sample is serially diluted from a range of neat to 1:1,000. An aliquot of each dilution is dispensed into separate wells of each of the first, second, and third series of wells. The plate is incubated at room temperature for time sufficient for the 16 (±4) and/or 30 (±4) kDa antigens, if present in the sample, to form a complex with the monoclonal antibody, usually 30 minutes to 2 hours. Afterwards, the wells are washed free of unbound material and a ligand-conjugated polyclonal or monoclonal antibody is added to each well. The plate is incubated for approximately 30 minutes or more at room temperature and then the unbound antibodies are washed from the wells. The monoclonal antibody-antigen-ligand-conjugated-antibody complex is detected by a detection method suitable to detect the ligand. The ligand can be a color producing ligand such as alkaline phosphatase or horseradish peroxidase, or a fluorescing compound such as FITC. Preferably, the above method is used to test serum or cerebrospinal fluid from the equine.

Since it is important to be able to test samples in the field for *Sarcocystis neuronaa*, the present invention further includes rapid immunodiffusion-based methods, their devices, and kits comprising the same. Therefore, the present invention can be provided as a kit comprising any one of the methods described in U.S. Pat. No. 5,620,845 to Gould et al., U.S. Pat. No. 5,559,041 to Kang et al., U.S. Pat. No. 5,656,448 to Kang et al., U.S. Pat. No. 5,728,587 to Kang et al., U.S. Pat. No. 5,695,928 to Stewart et al., U.S. Pat. No. 5,169,789 to Bernstein et al. U.S. Pat. No. 4,486, 530 to David et al., and U.S. Pat. No. 4,786,589 to Rounds et al. While the aforementioned disclose particular rapid immunodiffusion methods, the present invention is not to be construed to be limited to the aforementioned. It is within the scope of the present invention to embrace derivations and modifications of the aforementioned. Thus, in one embodiment of the kit, one or more monoclonal antibodies against one or more epitopes of one or both of the *Sarcocystis neurona* 16 (±4) and/or 30 (±4) kDa identifying antigens is immobilized on a membrane in a device designed for analyzing a biological sample. A biological sample is applied to the membrane which diffuses throughout the membrane. If the sample contains the identifying *Sarcocystis neurona* antigens, the identifying antigens will form a complex with the monoclonal antibodies on the membrane. Detection of the antibody-antigen complex is by a calorimetric method incorporated into the device, by immersing the device into a solution that causes a calorimetric reaction, or by reacting with a second monoclonal or polyclonal antibody conjugated to a reporter ligand.

While the above methods have been provided, other immunoassays are also within the scope of the present invention. For example, the present invention comprises an immunoassay comprising the 16 (±4) and/or 30 (±4) kDa antigen coupled to a reporter dye such as 6-carboxyfluorescein (FAM) or 6-carboxy-4,7,2',7'-tetrachlorofluorescein (TET) and an anti-16-and/or-30-kDa monoclonal antibody coupled to a quencher such as 6-carboxy-N,N,N',N'-tetramethylrhodamine. The quencher is attached to the monoclonal antibody such that when the labeled antigen binds the antibody, the quencher and reporter dye are in close proximity, and the reporter dye is prevented from fluorescing. Therefore, when a sample does not contain the 16 (±4) and/or 30 (±4) kDa antigen, all of the antigen is bound by the monoclonal antibody. Since the quencher and reporter dyes are in close proximity, the quencher prevents the reporter dye from fluorescing. However, when a sample contains the 16 (±4) and/or 30 (±4) kDa antigen, the 16 (±4) and/or 30 (±4) kDa antigen in the serum competes with the labeled 16 (±4) and/or 30 (±4) kDa antigen for the antibody, which results in some labeled 16 (±4) and/or 30 (±4) kDa antigen molecules remaining unbound. Because these unbound labeled 16 (±4) and/or 30 (±4) kDa antigen molecules are no longer in close proximity to the quencher on the antibody, the reporter dye on these labeled 16 (±4) and/or 30 (±4) kDa antigens will fluoresce. The intensity of the fluorescence is directly proportional to the amount of 16 and/or 30 kDa antigen in the sample. The advantage of this embodiment or variations of this embodiment which would be appreciated by those skilled in the art is that it can be performed in a small reaction volume and the results of the assay can be known instantaneously. Suitable devices for detecting the fluorescence include ELISA reading devices that detect the appropriate fluorescing wavelength, or spectrophotometers or fluorometers.

The present invention further provides a simplified, effective method for isolation, excystation, and culture of *Sarcocystis neurona* and other Sarcocystis spp. from an opossum or other animal and an improved method for isolation and culture of *Sarcocystis neurona* from equine. These methods are particularly useful for providing purified *Sarcocystis neurona* antigens for producing polyclonal or monoclonal antibodies, or for providing sufficient quantities of the organism from a biological sample from an equine to unequivocally determine whether an equine was infected with *Sarcocystis neurona.*

Thus, the isolation, excystation, and culture method from opossums and other animals is an important aspect of an embodiment of the antigen-capture immunoassay of the present invention useful for determining whether an opossum was infected with Sarcocystis neurona in an opossum wherein the amount of Sarcocystis neurona antigens obtainable from a biological sample is insufficient to determine the presence of Sarcocystis neurona in the opossum. The method involves the steps of mechanically disrupting a biological sample from an opossum in a physiological solution to make a homogenate. Preferably, the physiological solution is phosphate buffered saline (pH 7.4) and mechanical disruption is by a device such as a Dounce homogenizer. The homogenate is washed with the physiological solution and concentrated by low-speed centrifugation. The homogenate is then resuspended in a digestion solution consisting of pepsin-NaCl-HCl and incubated with frequent mixing at 37° C. for about 1.5 hours. Preferably, the pepsin-NaCl-HCl solution contains 0.65% pepsin (w/v), 0.86% NaCl (w/v), and 1% concentrated hydrochloric acid (v/v).

Afterwards, the semi-digest is washed with the physiological solution and resuspended in cell culture medium containing antibiotics until ready for culturing. Preferably, the culture medium is Hank's balanced salt solution containing penicillin (about 100 units per ml), amikacin (about 100 pg per ml), and amphotericin B (about 1.25 μg per ml).

For cell culturing, the semi-digest is concentrated by low-speed centrifugation, resuspended in a 2.6% hypochlorite solution, and stirred for about 1.5 hours at room temperature. Afterwards, the hypochlorite treated sample is concentrated by low-speed centrifugation and washed with the physiological solution. Next, the washed sample is concentrated and suspended in a digestion solution preferably consisting of 10% trypsin in an alkaline chelating solution (ACS) which consists of 100 mM NaCl, 3 mM KCl, 9 mM $Na_2HPO_4$, 3 mM Na-citrate, 0.5 mM $Na_2EDTA$, 0.1% glucose, 0.3% HEPES, 100 units per ml penicillin, and 1.25 μg per ml amphotericin B. After about 1.5 hours at 37° C., the sample is washed with the physiological solution, mechanically sheared and then applied to cell cultures of equine dermal cells. Preferably, the cell cultures are confluent and maintained in Dulbecco's modified Eagle's medium containing L-glutamine, 6% heat-inactivated fetal bovine serum, 100 units per ml penicillin, 100 μg per ml amikacin, and 1.25 μg per ml amphotericin B. The cultures are preferably incubated at 37° C. with 5% $CO_2$ and the culture medium changed every other day for about seven days, and then weekly thereafter. The cultures are monitored for evidence of Sarcocystis neurona infection, which usually appears by about the 14th day of culture. A suitable equine dermal cell line for culturing Sarcocystis neurona is the ATCC No. CCL-57 equine dermal cell line available from the American Type Culture Collection, 10801 University Boulevard, Manassas, Va. 20110.

The above cell line is also suitable for isolating Sarcocystis neurona from equines as well (Murphy et al., The Conference of Research Workers in Animal Diseases, Nov. 10–11, Chicago, Ill. (1997)). For example, neural tissue from spinal cord or brain are removed and placed in Hank's balanced salts containing antibiotics such as penicillin, amikacin, and amphotericin B and kept at room temperature. Preferably, within two hours of collection, portions of the tissue are minced and ground in a Dounce homogenizer with cell culture medium to make a slurry. Next, the slurry is poured onto confluent equine dermal cells such as ATCC No. CCL-57 and incubated preferably at 37° C. with 5% $CO_2$ for about 24 hours. The medium is replaced, and then replaced every other day for the first week, and then weekly thereafter. The cultures are monitored for evidence of Sarcocystis neurona infection, which usually appears about the 14th day of culture.

The aforementioned culturing methods enable sufficient Sarcocystis neurona to be available for producing the identifying antigens for making polyclonal or monoclonal antibodies for the immunoassay of the present invention, and for producing sufficient Sarcocystis neurona from a biological sample from an equine to enable identification using the immunoassay of the present invention.

An alternative method for concentrating Sarcocystis neurona antigens in serum and cerebrospinal fluid is using magnetic beads with bound Sarcocystis neurona monoclonal or polyclonal antibodies directed against the 16 (±4) and/or 30 (±4) kDa antigens. Using magnetic beads improves the sensitivity of the antigen test of the present invention. To perform the test, magnetic beads bound to Sarcocystis neurona monoclonal or polyclonal antibodies directed against the 16 (±4) and/or 30 (±4) kDa antigens are incubated with serum or cerebrospinal fluid samples from equines in a container 1for about 12 hours at 4° C. with stirring. Sarcocystis neurona 16 (±4) and/or 30 (±4) kDa antigens are bound by the antibodies forming an antibody-antigen complex. Afterwards, the magnetic beads are collected by placing a magnet around the container which causes the magnetic beads to be held to the sides of the container. This allows the sample fluid to be removed without loss of the magnetic beads with the bound antigens. After the sample fluid is removed, the magnetic beads with the bound antigens are washed with a buffer such as phosphate buffered saline, pH 7.4 (PBS). Next, the antigen is eluted from the antibodies and beads by removing the magnet and disrupting the antibody-antigen complex by mechanical agitation in PBS or by using a chaotropic reagent. The eluted and concentrated antigen can then be used in the antigen test method of the present invention.

Monoclonal antibodies that recognize and bind to particular epitopes of either the 16 (±4) and/or 30 (±4) kDa identifying antigens of Sarcocystis neurona are produced according to methods that are well known in the art. In particular, Sarcocystis neurona merozoites grown in culture were harvested, the antigens extracted, and the antigens separated using two-dimensional gel electrophoresis: isoelectric focusing followed by SDS-polyacrylamide gel electrophoresis, or other isolation methods which are well known in the art. The isolated identifying antigens are used to make monoclonal antibodies according to procedures well known in the art such as that described in Antibodies, A Laboratory Manual, eds. Harlow and Lane, Cold Spring Harbor Laboratory Press, Cold Spring Harbor, N.Y. (1988).

The hybridoma cell lines producing the monoclonal antibodies against the identifying antigens will be deposited at the American Type Culture Collection. The applicants' assignee acknowledges that the cell line cultures to be deposited are to be available for the life of the Pat. issued hereon, five years after the last request for a culture, or 30 years, whichever is longer.

While monoclonal antibodies can be made using hybridoma technologies well known in the art, the monoclonal antibodies against the identifying antigens can also be made according to phage display methods such as that disclosed in U.S. Pat. No. 5,977,322 to Marks et al. which is hereby incorporated herein by reference A phage display kit that is useful for making monoclonal antibodies is the Recombinant Phage Antibody System available from Amersham Pharmacia Biotech (Piscataway, N.J.).

Monoclonal antibodies produced by the aforementioned are used in the antigen-capture assay of the present invention, and further are used to identify cDNA clones in a cDNA expression library that express either the 16 (±4) and/or 30 (±4) kDa antigens.

Polyclonal antibodies can be made according to methods taught in *Antibodies, A Laboratory Manual*, eds. Harlow and Lane, Cold Spring Harbor Laboratory Press, Cold Spring Harbor, N.Y. (1988). For example, polyclonal antibodies can be made by inoculating rabbits, mice, goats, donkey, or horses with live or killed *Sarcocystis neurona* or the identifying 16 (±4) and/or 30 (±4) kDa antigens. The polyclonal antibodies are isolated from serum from the inoculated animal by ammonium sulfate precipitation to remove primarily the globulin. The precipitated antibodies are preferably further purified by anion exchange chromatography to remove most of the other proteins in the serum. Alternatively, the polyclonal antibodies can be isolated from the cerebrospinal fluid of an animal, preferably the horse, infected naturally or intentionally with live *Sarcocystis neuronaa*. Preferably, the antibodies from the cerebrospinal fluid are isolated or further purified by anion exchange chromatography. The purified antibodies are preferably stored in phosphate buffered saline at a neutral pH.

To facilitate making monoclonal and polyclonal antibodies against the identifying 16 (±4) and/or 30 (±4) kDa antigens, it is desirable to produce the 16 (±4) and 30 (±4) kDa antigens in vitro. In vitro production of the identifying antigens provides a rapid and simple means for obtaining large quantities of the antigens. Therefore, the genes from *Sarcocystis neurona* that encode the identifying 16 (±4) and/or 30 (±4) kDa antigens are also within the scope of the present invention. The genes encoding the 16 (±4) and/or 30 (±4) kDa antigens are identified using antibodies against *Sarcocystis neurona* conjugated to a reporter ligand to screen a cDNA expression library according to methods well known in the art. For example, replica plating screening methods can be used. To prevent the antibodies from binding to clones producing antigens other than the identifying antigens, the library is preincubated with bovine antibodies against *Sarcocystis cruzi* which will bind to clones producing antigens other than the identifying antigens. Thus, the only clones that are identified are clones expressing the identifying antigens. Since expression of certain *Sarcocystis neurona* antigens is stage specific, not only are cDNA expression libraries made from mRNA isolated from *Sarcocystis neurona* grown in culture but also *Sarcocystis neurona* at various stages of development, i.e., the merozoite, sporocyst, and sarcocyst stages.

Isolation of stage specific *Sarcocystis neurona* can be achieved according to the following method which demonstrates the collection of the intermediate host stage of *Sarcocystis neuronaa*. Brown headed cowbirds (Molothrus ater) are collected and euthanized and the carcasses chilled until needed. The muscles are dissected and observed for presence of Sarcocystis sarcocysts, which appear like grains of rice on the surface of the muscle. The sarcocysts are collected and extracted as follows. The muscle is sliced into small chunks and random samples are selected. Then 0.5 g of each sample is immersed in liquid nitrogen and pulverized in a mortar and pestle. Next 6 ml of digestion buffer is added which preferably consists of 100 mM NaCl, 10 mM Tris HCl, 25 mM EDTA, 0.5% sodium dodecyl sulfate, and 2 mg of proteinase K. The samples are incubated overnight in a shaker at 50° C. at 200×g. Next, the nucleic acids are removed from the sample by phenol extraction and recovered by precipitation with ethanol. The nucleic acids are tested for identity to *Sarcocystis neurona* using a *Sarcocystis neurona* specific PCR test using primers specific for *Sarcocystis neurona* SSURNA gene (Fenger et al., J. Parasitol. 81: 199–213 (1995)). The primers are the 3870R *Sarcocystis neurona* reverse primer 5'-CCATTCCGGACGCGGGT-3' (SEQ ID NO:1) and the 1055 eukaryote universal forward primer 5'-CGTGGTGCATGGCCG-3' (SEQ ID NO:2). These primers produce a 484 bp product when applied to a *Sarcocystis neurona* template. Another set of primers can be used to verify the presence of SSURNA DNA in each sample. These primers are the 3475R protist SSURNA reverse primer 5'-GCGCGTGCAGCCCAGAAC-3' (SEQ ID NO:3) and the universal primer (SEQ ID NO:2), which yields a 203 bp product. Samples which test positive for *Sarcocystis neurona* and no other Sarcocystis sp. are fed to pathogen-free opossums. About one month later after sporocysts are observed in the feces of the inoculated opossums, the mucosa of the small intestine is collected and used to inoculate equine dermal tissue culture cells as described previously. This method provides a means for providing samples of all of the stages of *Sarcocystis neurona* for use in development and verification of the method of the present invention.

Methods for screening cDNA expression libraries with antibodies are described in *Molecular Cloning: A Laboratory Manual, Second Edition*, edited by Sambrook et al. Cold Spring Harbor Laboratory Press, Cold Spring Harbor, N.Y. (1989). The expression library can be any plasmid-based expression library that uses a pUC, pUR, pEX or a lambda-based expression library. Preferably, the library is made using a ZAP EXPRESS vector (available from Stratagene, La Jolla, Calif.) which is a hybrid lambda-plasmid vector used to construct cDNA libraries. RNA is isolated using a Stratagene RNA isolation kit and cDNA is made using the ZAP EXPRESS cDNA Synthesis kit (available from Stratagene). The library is screened using antibodies against the 16 (±4) and/or 30 (±4) kDa identifying antigens and the picoBLUE Immunoscreening kit (available from Stratagene).

Once clones expressing the identifying antigens have been identified, a variety of methods suitable for producing the 16 and/or kDa antigens in large quantities sufficient are well known to those skilled in the art and are described in the prior art, e.g., in *Current Protocols in Molecular Biology*, section 3.8 (vol.1 1988) or *Molecular Cloning: A Laboratory Manual, Second Edition*, edited by Sambrook et al. Cold Spring Harbor Laboratory Press, Cold Spring Harbor, N.Y. (1989). For example, the DNA for genes encoding the 16 (±4) and/or 30 (±4) kDa antigens are inserted into a plasmid expression vector according to methods well known to the art. The plasmid vector provides a promoter for transcribing the genes into RNA which is then translated into the antigen. The promoter can be a constitutive promoter, a phage promoter, or an inducible promoter such as the lacZ promoter. To produce the antigens, bacteria such as *E. coli* are transformed with the plasmid vector. Methods for producing large quantities of antigens in bacterial expression systems are well known in the art.

While bacterial methods are used to produce the 16 (±4) and/or 30 (±4) kDa antigens, it can be desirable to produce the antigens in a eukaryote expression system. A particularly useful system for expressing the 16 (±4) and/or 30 (±4) kDa antigens is the baculovirus expression system which is disclosed in U.S. Pat. No. 5,229,293 to Matsuura et al. which is hereby incorporated herein by reference. Baculovirus expression vectors suitable to produce the 16 (±4) and/or 30 (±4) kDa antigens are the pPbac and pMbac vectors from Stratagene; and the Bac-N-Blue vector, the pBlueBac4.5 vector, pBlueBacHis2-A,B,C, and the pMelBac available from Invitrogen, Carlsbad, Calif.

Another eukaryote system useful for expressing the 16 (±4) and/or 30 (±4) kDa antigens is a yeast expression system such as the ESP Yeast Protein Expression and Purification System available from Stratagene. Another yeast expression system is any one of the Pichia-based Expression systems from Invitrogen. Mammalian expression systems are also embraced by the present invention. Examples of mammalian expression systems are the LacSwitch II system, the pBK Phagemid, pXT1 vector system, and the pSG5 vector system from Stratagene; the pTargeT mammalian expression vector system, the pSI mammalian expression vector, pCI mammalian expression vector, and pAdVantage vectors available from Promega Corporation, Madison, Wis.; and the Ecdysone-Inducible Mammalian Expression System, pCDM8, pcDNA1.1, and pcDNA1.1/ Amp available from Invitrogen.

Another method for producing the 16 (±4) and/or 30 (±4) kDa antigens in a eukaryote expression system is to insert the DNA encoding the 16 (±4) and/or 30 (±4) kDa antigens into the genome of the eukaryote cell or in a eukaryote virus expression vector such as herpesvirus, poxvirus, or adenovirus to make a recombinant virus that expresses the 16 (±4) and/or 30 (±4) kDa antigens. The recombinant virus vectors are used to infect mammalian cells wherein the 16 and/or 30 kDa antigens are produced in the cell. The 16 (±4) and/or 30 (±4) kDa antigens can be purified using methods well known in the art for purifying antigens. U.S. Pat. No. 5,223,424 to Cochran et al. which is hereby incorporated herein by reference provides methods for inserting genes into herpesvirus expression vectors such as equine herpesvirus. U.S. Pat. Nos. 5,338,683 and 5,494,807 to Paoletti et al. and U.S. Pat. No. 5,935,777 to Moyer et al. which are hereby incorporated herein by reference provide methods for inserting genes into poxvirus expression vectors such as vaccinia virus, entomopoxvirus, and canary poxvirus. In another embodiment, the genes encoding the 16 (±4) and/or 30 (±4) kDa antigens can be inserted into a defective virus such as the herpesvirus amplicon vector which is disclosed in U.S. Pat. No. 5,928,913 to Efstathiou et al. which is hereby incorporated herein by reference. In any of the aforementioned virus vectors, the genes encoding the 16 (±4) and/or 30 (±4) kDa antigens are operably linked to a eukaryote promoter at the 5' end of the DNA encoding the antigen and a eukaryote termination signal and poly(A) signal located at the 3' end of the gene. Examples of such promoters are the cytomegalovirus immediate-early (CMV) promoter, the Rous sarcoma virus long terminal repeat (RSV-LTR) promoter, the simian virus 40 (SV40) immediate-early promoter, and inducible promoters such as the metallothionein promoter. An example of a DNA having a termination and poly(A) signal is the SV40 late poly(A) region. Another example of a viral expression system suitable for producing the 16 (±4) and/or 30 (±4) kDa antigens of the present invention is the Sindbis Expression system available from Invitrogen. The use of these commercially available expression vectors and systems are well known in the art.

The following examples are intended to promote a further understanding of the present invention.

EXAMPLE 1

This example is to demonstrate the preparation of monoclonal antibodies that recognize and react to the 16 (±4) and/or 30 (±4) kDa identifying antigens of *Sarcocystis neurona.*

*Sarcocystis neurona* was cultured on equine dermal cell line cultures as taught in Example 5 or on bovine monocyte cell cultures as taught by Granstrom et al., *J. Vet. Diagn. Invest.* 5: 88–90 (1993). *Sarcocystis neurona* merozoites were harvested and the 16 (±4) and/or 30 (±4) kDa antigens purified by methods known to the art for purifying antigens, i.e., the 16 (±4) and/or 30 (±4) kDa antigens were purified from merozoites by two-dimensional polyacrylamide gel electrophoresis. Then the purified antigens are used to make monoclonal antibodies according to the methods in *Antibodies, A Laboratory Manual*, eds. Harlow and Lane, Cold Spring Harbor Laboratory Press, Cold Spring Harbor, N.Y. (1988), well known to those skilled in the art as a source for methods for making polyclonal and monoclonal antibodies.

BALB/c mice are immunized with an initial injection of 1.0 $\mu$g of the 16 (±4) or 30 (±4) kDa identifying antigen per mouse mixed 1:1 with Titer max, Freund's incomplete adjuvant or Freund's complete adjuvant. After two weeks, a booster injection of 1.0 Δg of antigen is injected into each mouse intravenously without adjuvant. Three days after the booster injection a fusion is performed with a mouse myeloma cell line. Mid log phase myeloma cells are harvested on the day of fusion, checked for viability, and separated from the culture medium by low-speed centrifugation. Then the cells are resuspended in serum-free Dulbecco's Modified Eagle's medium (DMEM).

The spleens are removed from the immunized mice and washed three times with serum-free DMEM and placed in a sterile Petri dish containing 20 ml of DMEM containing 20% fetal bovine serum, 1 mM pyruvate, 100 units penicillin, and 100 units streptomycin. The cells are released by perfusion with a 23 gauge needle. Afterwards, the cells are pelleted by low-speed centrifugation and the cell pellet is resuspended in 5 ml 0.17 M ammonium chloride and placed on ice for several minutes. Then 5 ml of 20% bovine fetal serum is added and the cells pelleted by low-speed centrifugation. Afterwards, the cells are resuspended in 10 ml DMEM and mixed with myeloma cells to give a ratio of 3:1. The cell mixture is pelleted by low-speed centrifugation, the supernatant fraction removed, and the pellet allowed to stand for 5 minutes. Next, over a period of 1 minute, 1 ml of 50% polyethylene glycol (PEG) in 0.01 M HEPES pH 8.1 at 37° C. is added. After 1 minute incubation at 37° C., 1 ml of DMEM is added for a period of another 1 minute, then a third addition of DMEM is added for a further period of 1 minute. Finally, 10 ml of DMEM is added over a period of 2 minutes. Afterwards, the cells are pelleted by low-speed centrifugation and the pellet resuspended in DMEM containing 20% fetal bovine serum, 0.016 mM thymidine, 0.1 hypoxanthine, 0.5 $\mu$M aminopterin, and 10% hybridoma cloning factor (HAT medium). The cells are then plated into 96-well plates.

After 3, 5, and 7 days half the medium in the plates is removed and replaced with fresh HAT medium. After 11 days, the hybridoma cell supernatant is screened by an ELISA assay or a Western blot as previously described. In the ELISA assay, 96-well plates are coated with the appropriate identifying antigen. One hundred $\mu$l of supernatant from each well is added to a corresponding well on a screening plate and incubated for 1 hour at room temperature. After incubation, each well is washed three times with water and 100 $\mu$l of a horseradish peroxide conjugate of goat anti-mouse IgG (H+L), A, M (1:1,500 dilution) is added to each well and incubated for 1 hour at room temperature. Afterwards, the wells are washed three times with water and the substrate OPD/hydrogen peroxide is added and the reaction is allowed to proceed for about 15 minutes at room temperature. Then 100 $\mu$l of 1 M HCl is added to stop the reaction and the absorbance of the wells is measured at 490 nm. Cultures that have an absorbance greater than the control wells are removed to 2 cm² culture dishes, with the addition of normal mouse spleen cells in HAT medium. After a further three days, the cultures are rescreened as above and those that are positive are cloned by limiting dilution. The cells in each 2 cm² culture are counted and the cell concentration adjusted to $1 \times 10^5$ cells per ml. The cells are diluted in complete medium and normal mouse spleen cells are added. The cells are plated in 96-well plates for each dilution. After 10 days, the cells are screened for growth. The growth positive wells are screened for antibody production those testing positive are expanded to 2 cm² cultures and provided with normal mouse spleen cells. This cloning procedure is repeated until stable antibody producing hybridomas are obtained. Then the identified stable hybridomas are progressively expanded to larger culture dishes to provide stocks of the cells.

Production of ascites fluid is performed by injecting intraperitoneally 0.5 ml of pristane into female mice to prime the mice for ascites production. After 10 to 60 days, $4.5 \times 10^6$ cells is injected intraperitoneally into each mouse and ascites fluid is harvested between 7 and 14 days later. Alternatively, the hybridoma cells are grown in culture according to methods well known in the art for cultivating hybridoma cells for antibody production.

An alternate method for screening hybridomas for antibody production is as follows. *Sarcocystis neurona* is heat-denatured in 0.5 M Tris (pH 7.4) with 10% SDS, 20% glycerol and 5% 2-mercaptoethanol. The denatured antigens are separated by SDS-polyacrylamide gel electrophoresis in a 12–20% (v/v) linear gradient gel with a 4% (v/v) stacking gel. The separated antigens are electrophoretically transferred to PVDF membranes at 100 volts for 1.5 hours, then 150 volts for 0.5 hours. The membranes are then blocked overnight in 1% by volume bovine serum albumen in 0.5% Tween-Tris buffered saline (Blocking buffer). The blots are air-dried and stored frozen. Prior to use, the membranes are incubated with bovine serum albumen and *Sarcocystis cruzi* antibodies in Blocking buffer at a range of 1:10 to 1:100 ratio for two hours. Afterwards, the membranes are washed in 0.5% Tween-Tris buffered saline and then incubated with monoclonal antibodies from the various hybridoma clones. The membranes are developed as disclosed in the prior art, e.g., Granstrom et al., J. Vet. Diag. Invest. 5: 88–90 (1993) or *Antibodies, A Laboratory Manual*, eds. Harlow and Lane, Cold Spring Harbor Laboratory Press, Cold Spring Harbor, N.Y. (1988).

Hybridomas that successfully produce monoclonal antibodies against various epitopes of the 16 (±4) and 30 (±4) kDa identifying antigens are expanded as above, and used to make monoclonal antibodies for the antigen-based immunoassay and for identifying cDNA library clones in Example 2 that contain *Sarcocystis neurona* DNA which express either the 16 (±4) and/or 30 (±4) kDa antigens.

In the foregoing procedure, monoclonal antibodies against particular epitopes of the identifying antigens are produced.

EXAMPLE 2

This example illustrates a method for the construction of a CDNA library that expresses the 16 (±4) and/or 30 (±4) kDa antigens of *Sarcocystis neuronaa*. The methods for making and screening cDNA expression libraries are well known to those skilled in the art and are described in *Molecular Cloning: A Laboratory Manual, Second Edition*, edited by Sambrook et al. Cold Spring Harbor Laboratory Press, Cold Spring Harbor, N.Y. (1989). Polyclonal or monoclonal antibodies made as in Example 1 are used to screen the library for clones that express the 16 (±4) and/or 30 (±4) kDa identifying antigens. When polyclonal antibodies are used, the clones are preincubated with polyclonal antibodies against *Sarcocystis cruzi* to prevent binding of *Sarcocystis neurona* antibodies to any clone except for the clones expressing the identifying antigens.

EXAMPLE 3

This Example describes an ELISA-based assay kit for detecting the 16 (±4) and/or 30 (±4) kDa antigens (antigens) in serum or cerebrospinal fluid from an equine. The assay demonstrates that a kit in the standard ELISA microtiter plate format is useful for detecting antigens in equine serum or cerebrospinal fluid that bind to the monoclonal antibodies made in Example 1 against the 16 (±4) and/or 30 (±4) kDa antigen.

A series of wells of a microtiter plate are coated with monoclonal antibodies made against the 16 (±4) and/or 30 (±4) kDa antigen as in Example 1, a series of wells are coated with bovine serum albumen for the negative control, and a series of wells are coated with antigens for the positive control. The antigens are affixed to the wells using methods well known in the art to immobilize antigens to microtiter wells. Such methods are disclosed in *Antibodies, A Laboratory Manual*, eds. Harlow and Lane, Cold Spring Harbor Laboratory Press, Cold Spring Harbor, N.Y. (1988) which is hereby incorporated herein by reference.

Equine serum or cerebrospinal fluid, both neat and serially diluted from 1:5 to 1:500 in Binding Buffer (10 mM Tris pH 8.0, 500 mM NaCl, 0.1% Nonidet P-40, 1% non-fat dry milk) are dispensed into sample wells of the microtiter μlate. The microtiter μlate is incubated for approximately 30 minutes to an hour at room temperature. The unbound material is removed by three successive washes with Wash Buffer (10 mM Tris pH 8.0, 10 mM NaCl, 1% non-fat dry milk). Next, alkaline phosphatase conjugated monoclonal antibody against the 16 (±4) and/or 30 (±4) kDa antigens in Binding Buffer is added to the wells. The microtiter plate is incubated from 30 minutes to an hour at room temperature. Afterwards, the unbound monoclonal antibody is removed with three successive washes with Wash Buffer. Next, Reaction Buffer containing p-nitrophenyl phospahte (pNPP) in 0.1 M Tris pH 9.0 is added to the well and the plate incubated in the dark at room temperature for approximately 30 minutes or until the color reaction develops a yellow color in the positive control wells whereas the negative control wells do not develop a yellow color (PNPP is available as a kit for immunodetection from Sigma Chemicals, Inc., St. Louis, Mo.). Therefore, when the serum or cerebrospinal fluid contains either the 16 (±4) and/or 30 (±4) kDa antigens, a yellow color forms in the sample wells.

Alternatively, the ELIZA can use 5-bromo-4-chloro-3-indolyl phosphate/nitro blue tetrazolium (BCIP/NBT) as the color indicator. In which case, if a sample contains *Sarcocystis neurona* antigens, a blue-purple precipitate is formed. In an alternate embodiment further still, the antibodies are conjugated to horseradish peroxidase and the color indicator is selected from the group consisting of 2,2'-azino-bis(3-ethylbenz-thiazoline-6-sulfonic acid (ABTS), 0-phenylenediamine (OPD), 3,3',5,5'-tetramethylbenzidine (TMB), odianisidine, and 5-aminosalicyclic acid (5AS), which provides in wells positive for *Sarcocystis neurona* antigens, green, orange, blue, yellow-orange, or brown, respectively.

EXAMPLE 4

A diagnostic assay based on a dip stick device for detecting the 16 (±4) and/or 30 (±4) kDa antigens in serum or cerebrospinal fluid of equines is disclosed.

Monoclonal antibodies made according to Example 1 are immobilized to a solid phase support according to any one of U.S. Pat. No. 5,620,845 to Gould et al., U.S. Pat. No. 5,559,041 to Kang et al., U.S. Pat. No. 5,656,448 to Kang et al., U.S. Pat. No. 5,728,587 to Kang et al., U.S. Pat. No. 5,695,928 to Stewart et al., U.S. Pat. No. 5,169,789 to Bernstein et al. U.S. Pat. No. 4,486,530 to David et al., and U.S. Pat. No. 4,786,589 to Rounds et al.

Serum or cerebrospinal fluid is applied to the device and allowed to diffuse throughout the device. Serum or cerebrospinal fluid containing the 16 (±4) and/or 30 (±4) kDa antigens form an antibody-antigen complex with the immobilized monoclonal antibodies whereas serum from an equine that does not contain the 16 (±4) and/or 30 (±4) kDa antigens does not form an antibody-antigen complex. The antibody-antigen complex is detected as described in U.S. Pat. No. 5,620,845 to Gould et al., U.S. Pat. No. 5,559,041 to Kang et al., U.S. Pat. No. 5,656,448 to Kang et al., U.S. Pat. No. 5,728,587 to Kang et al., U.S. Pat. No. 5,695,928 to Stewart et al., U.S. Pat. No. 5,169,789 to Bernstein et al. U.S. Pat. No. 4,486,530 to David et al., or U.S. Pat. No. 4,786,589 to Rounds et al.

EXAMPLE 5

This example provides a simplified method for the isolation, excystation, and culture of Sarcocystis species using opossums as a model. The method is an improvement over the isolation, excystation and culture methods of the prior art.

Twenty-seven opossums from southern Michigan were humanely killed and their intestines screened for Sarcocystis spp. oocysts between Ap. 1996 and Mar. 1998. In addition, *Sarcocystis oocysts* collected from wild grackle (Quiscalus sp.) fed opossums and oocysts collected from wild-caught cowbird (*Molothrus ater*) fed to opossums in the inventors' laboratory were tested. A 2-cm segment of mid-small intestine from each animal was removed and washed with 0.01 M phosphate-buffered saline, pH 7.4 (PBS). A scraping of mucosa was observed at 100×magnification using a Nikon Optiphot-2 microscope to determine the presence or absence of oocysts. Feces from the large intestine was removed from each positive animal and tested for the presence of Sarcocystis spp. sporocysts and other parasite ova by sucrose flotation according to Sloss et al., In *Veterinary Clinical Parasitology*, Iowa State University Press, Ames, Iowa, (1994), p. 198. The small intestine was flushed with PBS to remove contents and slit lengthwise. The mucosa was scraped off with a glass slide and ground in a Dounce homogenizer. The slurry was transferred to a conical tube and washed three times with PBS by centrifugation for 10 minutes at 500×g. The pellet was resuspended in 3 volumes of pepsin-NaCl-HCl (0.65% pepsin w/v, 0.86% NaCl w/v, 1% concentrated HCl v/v) and incubated at 37° C. for 1.5 hours with frequent mixing. The slurry was washed 3 times with PBS as above and the pellet stored in Hank's balanced salt solution (HBSS) plus penicillin (100 units/ml), amikacin (100 µg/ml), and amphotericin B (1.25 µg/ml) until further use. A 1 to 3 ml aliquot of the semidigested mucosa was concentrated by centrifugation for 10 minutes at 500×g. The pellet was suspended in 15 ml of 2.6% sodium hypochlorite solution, stirred for 1.5 hours at room temperature, and washed once with PBS as above.

The improvement in the excystation and culture of Sarcocystis sp. over the prior art is the mechanical excystation step as set forth below. The washed sodium hypochlorite pellet was suspended in 15 ml 10% trypsin in alkaline chelating solution (ACS) which is a solution that consisted of 100 mM NaCl, 3 mM KCl, 9 mM $Na_2HPO_4$, 3 mM Na-citrate, 0.5 mM $Na_2EDTA$, 0.1% glucose, 0.3% HEPES, 100 units penicillin, and 1.25 µg/ml amphotericin B, and incubated 1.5 hour at 37° C. After washing once with PBS as above, a drop of the pellet was compressed between sterile slides and shearing forces were applied by moving the slides back and forth. The material on the slides was washed with cell medium into flasks of confluent equine dermal cells (ATCC CCL-57, freely available from the American Type Culture Collection, 10801 University Boulevard, Manassas, Va. 20110-2209) in Dulbecco's modified Eagle's medium (DMEM; available from GIBCO a division of Life Technologies, Bethesda, MD) plus L-glutamine, 6% heat-inactivated fetal bovine serum, penicillin (100 units/ml), amikacin (100 µg/ml), and amphotericin B (1.25 µg/ml). *Sarcocystis neurona* isolated from neural tissue of EPM-affected horses could be passaged continuously long term on this cell line. Before and after inoculation, equine dermal cells were grown at 37° C. with 5% $CO_2$, with medium changed every other day for 7 days and weekly thereafter. After inoculation, cultures were observed weekly for evidence of cellular damage due to Sarcocystis spp. replication and for the presence of extracellular merozoites using an Olympus CK2 inverted microscope. Positive cultures were confirmed by Romanowsky (modified Giemsa-Wright)-stained cytospin of infected cells using a Shandon Cytospin 3 centrifuge and a Wescor 7100 Aerospray slide stainer. Separate sterile pipettes were used to add or withdraw media from each flask containing each separate strain to eliminate the possibility of cross contamination.

Isolation, excystation, and culture of opossum Sarcocystis spp. by the improved method shown herein resulted in viable organisms for all 7 animals that had sporocysts detected in the feces. All of these opossums were adult males, 6 from the same Michigan farm on which two horses had been diagnosed with histopathologically confirmed EPM. Each opossum harbored a million or more oocysts in the small intestinal mucosa; however, fewer than two sporocysts per gram of feces were observed in each when feces from the large intestine was tested by sucrose flotation. Ascarid, strongyle, tapeworm, Capillaria sp., Physaloptera sp. eggs, or a combination of these eggs were also observed in the wild-caught animals.

Processing the mucosa with a Dounce homogenizer and subsequent pepsin-NaCl-HCl digestion broke down tissues but did not disrupt *Sarcocystis oocysts*, many of which were still attached to tissue fragments. Further digestion with sodium hypochlorite freed most of the oocysts and released many sporocysts. Three chemical excystation methods as set forth in Comparative Example 1 were attempted. All were effective in breaking down the oocyst walls and weakening the sporocyst walls, but none to few excysted sporocysts were detected afterward. However, mechanical excystation as performed according to the improvement shown herein proved to be most effective, especially with the 10% trypsin ACS pretreated sporocysts.

Processed small intestine from the first opossum isolate refrigerated in HBSS plus penicillin, streptomycin, and amphotericin B remained contaminated with bacteria. Inoculation of dermal cells with this contaminated material resulted in cell death. Culture and sensitivity testing proved the contaminating organism to be Alcalcigens sp. Amikacin (100 µg/ml) was substituted for the streptomycin in the mucosal preparation and in all subsequent solutions, including the cell growth media. Amikacin killed the contaminant and no bacterial contamination of any subsequent isolates using the penicillin-amikacin-amphotericin B-enhanced media.

Successful culture of merozoites from the first opossum isolate occurred in 13 of 15 flasks into which sporocysts pretreated with 10% trypsin in ACS and mechanically excysted by the improved method herein were inoculated. In contrast, 4 flasks each were inoculated with the three different regimes of chemically excysted sporocysts without mechanical excystation as shown in Comparative Example 1. All remained negative except for 1 trypsin-ACS- and 1 bile-trypsin-pretreated inoculum.

Thus, the trypsin-ACS/mechanically excysted sporocysts made as above infected more efficiently than those prepared by chemical methods; each flask became positive by visual examination at about 10 to 30 sites between about 5 to 15 days after inoculation. In contrast, the trypsin-ACS pretreated sporocysts became positive in culture 14 days after inoculation and at one site, and the bile-trypsin-pretreated sporocysts became positive in culture 26 days after inoculation at only one site. Successful culture was further confirmed by Romanowsky-stained cytospin of infected cells. All flasks negative for merozoites visually and by Romanowsky-stained cytospin of cells were discarded eight weeks after inoculation because longer term culture did not result in more positive flasks in preliminary trials. The mechanical excystation method has been used for all subsequent opossum isolates. The six additional isolates became positive using microscope visualization from 6 to 14 days after inoculation at many sites in each flask. All strains isolated from these seven opossums have grown well long term (six months or longer).

Sporocysts collected from six specific pathogen-free opossums fed wild-caught cowbird were successfully excysted and grown in equine dermal cell culture in our laboratory using this technique as were sporocysts thought to be *Sarcocystis falcatula* from opossums fed wild-caught grackle (these were wild-caught opossums testing negative for Sarcocystis by fecal flotation for three weeks prior to infection). The cowbird isolates have grown well long term in equine dermal cells. Marsh et al., J Parasitology 83: 1189–1192 (1997) have shown that an equine-derived *Sarcocystis neurona* isolate grew highly efficiently long term in equine dermal cells. The grackle-fed opossum isolate (*Sarcocystis falcatula*) grew in equine dermal cells but only for a brief time, 3 to 8 weeks in three different infection trials. Although the cell line was not effective for long-term growth of this Sarcocystis sp., the excystation method and initial culture were successful.

Thus, this example shows that multiple isolates of merozoites have been successfully cultured from opossum-derived Sarcocystis spp. oocysts using the improved method of digestion followed by manual excystation. Long-term growth of all opossum Sarcocystis spp. should be possible using the improvement and the appropriate cell line. Equine dermal cells work well for *Sarcocystis neuronaa*, but other cell lines may be more useful for other Sarcocystis spp. A more complete understanding of the life cycle of *Sarcocystis neurona* and, therefore; of the factors that determine exposure of horses should be possible using the opossum isolates derived from the above excystation and culture methods.

EXAMPLE 6

This example provides three chemical excystation methods for preparing Sarcocystis sp. oocysts. The chemically prepared samples were compared to samples prepared by the improved method shown in Example 5.

Samples were prepared as in Example 5 except that after washing the pellet that had been suspended in 2.6% sodium hypochlorite, the samples were treated with either (1) 10% trypsin in ACS, (2) 10% bile and 2% trypsin in HBSS (Speer et al., J Protozoology 33: 486–490 (1986)), or 5% sodium taurocholate and 2% trypsin in PBS (Speer et al., ibid.). All the samples were incubated at 37° C. and 5% $CO_2$. The chemical methods provided poor results even though the methods were effective in breaking down the oocyst walls and weakening the sporocyst walls.

Flasks inoculated with samples from the three above chemically excysted sporocysts remained negative except for one trypsin-ACS- and one bile-trypsin-pretreated inoculum. The trypsin-ACS-pretreated sporocysts became positive in culture 14 days after inoculation in one site and the bile-trypsin-pretreated sporocysts became positive in culture 26 days after inoculation at one site. In contrast, the improved method as was shown in Example 5 was more efficient. Each flask became positive by visual examination at many sites 5 to 15 days post-inoculation.

EXAMPLE 7

This examples shows the isolation of stage specific *Sarcocystis neurona* according to the following method which demonstrates the collection of intermediate stage *Sarcocystis neurona*.

Brown headed cowbirds (*Molothrus ater*) were collected from a joint project of the Michigan Department of Natural Resources and the United States Fish and Wildlife Service trapping program in the Huron National Forest of Michigan. The government officials humanely euthanized the birds, chilled their bodies, and provided the bodies for biology research. The muscles were dissected from the bird carcasses and observed for presence of *Sarcocystis sarcocysts*, which appear like grains of rice on the surface of the muscle. The sarcocysts were collected and extracted as follows.

The muscle was sliced into small chunks and random samples were selected. Then 0.5 g of each sample was immersed in liquid nitrogen and pulverized in a mortar and pestle. Next 6 ml of digestion buffer was added consisting of 100 mM NaCl, 10 mM Tris HCl, 25 mM EDTA, 0.5% sodium dodecyl sulfate, and 2 mg of proteinase K (Boehringer-Mannheim). The samples were incubated overnight in a shaker at 50° C. at 200×g. Next, the samples were organically extracted using an equal volume of 25:24:1 phenol:chloroform:isoamyl alcohol and centrifuged at 2,000×g for 10 minutes. The aqueous phase was removed and the nucleic acids were precipitated from the aqueous phase by addition of 3 ml of 7.5 M ammonium acetate and 4 volumes of 100% ethanol at −20° C. and immediately centrifuged at 12,900×g for 45 minutes at 0° C. The supernatant fraction was removed and the nucleic acid pellet washed with 3–4 ml of 70% ethanol, then centrifuged at 12,900×g for 5–10 minutes. The supernatant fraction was removed and the nucleic acid pellet was air-dried before dissolving the nucleic acid pellet in Tris HCl- EDTA buffer at pH 8.0 to make a nucleic acid solution.

The nucleic acid solutions from the sarcocysts were tested for identity to *Sarcocystis neurona* using a *Sarcocystis neurona* specific PCR test using primers specific for *Sarcocystis neurona* SSURNA gene. The primers were the 3870R *Sarcocystis neurona* reverse primer, 5'-CCATTCCGGACGCGGGT-3' (SEQ ID NO:1), and the 1055 eukaryote universal forward primer, 5'-CGTGGTGCATGGCCG-3' (SEQ ID NO:2). These primers produced a 484 bp product when applied to a *Sarcocystis neurona* template. Another set of primers were used to verify the presence of SSURNA DNA in each sample. These primers were the 3475R protist SSURNA reverse primer, 5'-GCGCGTGCAGCCCAGAAC-3' (SEQ ID NO:3), and the universal primer (SEQ ID NO:2), which yielded a 203 bp product. The PCR was optimized for annealing temperature and $MgCl_2$ concentration using five 10-fold dilutions of DNA made from $1\times10^5$ to $1\times10^1$ merozoites in a sample to determine sensitivity. Annealing temperature was varied between 57 and 64° C. $MgCl_2$ concentration was tested at 1, 2, 3, and 4 mM. Samples which tested positive for *Sarcocystis neurona* and no other Sarcocystis sp. were fed to pathogen-free opossums. About one month later sporocysts were collected from the small intestine of the inoculated opossums and used to inoculate equine dermal tissue culture cells as descibed previously.

This method provides a means for providing samples of all of the stages of *Sarcocystis neurona* for use in development and verification of the method of the present invention.

EXAMPLE 8

This example provides a method of producing polyclonal antibodies against *Sarcocystis neurona* from cerebrospinal fluid.

Horses with signs compatible with EPM and positive by Western blot test results of serum and cerebrospinal fluid are humanely euthanized with an overdose of barbiturate anethesia given in the juglar vein using a catheter. The horse's throat is opened posterior to the maxilla until the dura mater membrane is observed ventrally at the atlantooccioital joint space. An 18 guage needle connected to a 60 ml syringe is used to puncture the membrane and withdraw the cerebrospinal fluid in a manner to exclude contamination with blood. Upwards of 400 ml of cerebrospinal fluid can be removed which can be stored at −20° C. until needed. Once the horses are confirmed to have *Sarcocystis neurona* using culture to grow the parasite from the central nervous tissue, the cerebrospinal fluid sample is thawed, pooled with samples from other horses and the IgG antibodies precipitated using ammonium sulfate, typically at a saturation level of about 50%. Aimonium sulfate precipitation methods are well known in the art.

Alternatively, the antibodies can also be purified by ion-exchange chromatography, either batch or column. Two alternative methods can be used. In the first, the pH is kept below the isoelectric point for most antibodies, and therefore the antibodies will not bind to an anion exchange resin such as DEAE cellulose. In the second approach, the pH is raised above the isoelectric point where the antibodies will bind the anion exchange resin. As the salt concentration is raised, the antibodies will be the first of the molecules to elute. It is preferable that the ion-exchange chromatography be performed instead of ammonium sulfate precipitation when the antibodies are from cerebrospinal fluid.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the Claims attached herein.

We claim:

1. In a method for detecting the presence of *Sarcocystis neurona* in an equine in an immunoassay, the improvement which comprises reacting a biological sample from the equine suspected of harboring the *Sarcocystis neurona* with at least one isolated antibody specific for a 16 (±4) kDa *Sarcocystis neurona* antigen and at least one isolated antibody specific for a 30 (±4) kDa *Sarcocystis neurona* antigen, wherein each antibody binds its respective antigen to form an antibody-antigen complex.

2. The method of claim 1, wherein the antibody-antigen complex is detected with a labeled antibody against the antigen or the antibody in the antibody-antigen complex.

3. The method of claim 2 wherein the label is selected from the group consisting of alkaline phosphatase, horseradish peroxidase, fluorescent compounds, luminescent compounds, colloidal gold, and magnetic particles.

4. The method of claim 2 wherein the label is biotin which is reacted with peroxidase conjugate and then detected by reaction with an appropriate color forming substrate.

5. The method of any one of claims 1, 2, 3, or 4 wherein the biological sample is selected from the group consisting of serum, cerebrospinal fluid, and cell culture fluid from equine dermal cells infected with *Sarcocystis neurona* from a biological sample.

6. The method of claim 1 wherein the antibody against the antigen is immobilized on a support selected from the group consisting of a membrane or a plate.

7. In a method for detecting the presence of *Sarcocystis neurona* in an equine in an immunoassay, the improvement which comprises reacting a biological sample from the equine suspected of harboring the Sarcocystis neurona with at least one monoclonal or isolated polyclonal antibody specific for a 16 (±4) kDa *Sarcocystis neurona* antigen and at least one monoclonal or isolated polyclonal antibody specific for a 30 (±4) kDa *Sarcocystis neurona* antigen, wherein each monoclonal antibody binds its respective antigen to form an antibody-antigen complex.

8. The method of claim 7 wherein the antibody-antigen complex is detected with a labeled antibody against the antigen or the antibody in the antibody-antigen complex.

9. The method of claim 8 wherein the label is selected from the group consisting of alkaline phosphatase, horseradish peroxidase, fluorescent compounds, luminescent compounds, colloidal gold, and magnetic particles.

10. The method of claim 8 wherein the label is biotin which is reacted with peroxidase conjugate and then detected by reaction with an appropriate color forming substrate.

11. The method of any one of claims 7, 8, 9, or 10 wherein the biological sample is selected from the group consisting of serum, cerebrospinal fluid, and cell culture fluid from equine dermal cells infected with a biological sample.

12. The method of claim 7 wherein the monoclonal antibody against the antigen is immobilized on a support selected from the group consisting of a membrane or a plate.

13. The method of claim 8 wherein the labeled antibody is a second monoclonal antibody.

14. A method for detecting *Sarcocystis neurona* in an immunoassay comprising:

(a) reacting a biological sample from an equine suspected of harboring the *Sarcocystis neurona* with at least one monoclonal antibody specific for a 16 (±4) kDa *Sarcocystis neurona* antigen and at least one monoclonal antibody specific for a 30 (±4) kDa *Sarcocystis neurona* antigen wherein each monoclonal antibody is immobilized on a support and wherein each monoclonal antibody binds its respective antigen to form a complex, and (b) detecting the complex.

15. The method of claim 14 wherein the complex is detected by a labeled antibody against the antigen or monoclonal antibody in the complex.

16. The method of claim 15 wherein the labeled antibody is a second monoclonal antibody.

17. The method of claim 15 or 16 wherein the label is selected from the group consisting of alkaline phosphatase, horseradish peroxidase, fluorescent compounds, luminescent compounds, colloidal gold, and magnetic particles.

18. The method of claim 17 wherein the label is biotin which is reacted with peroxidase conjugate and then detected by reaction with an appropriate color forming substrate.

19. The method of claim 14 wherein the biological sample is selected from the group consisting of serum, cerebrospinal fluid, and cell culture fluid from equine dermal cells infected with *Sarcocystis neurona* from a biological sample.

20. The method of claim 14 wherein the monoclonal antibody against the antigen is immobilized on the support selected from the group consisting of a membrane or a plate.

21. A kit for detecting *Sarcocystis neurona* in a biological sample from an equine comprising:

(a) at least one monoclonal or isolated polyclonal antibody against a 16 (±4) kDa *Sarcocystis neurona* antigen and at least one monoclonal or isolated polyclonal antibody against a 30 (±4) kDa *Sarcocystis neurona* antigen, wherein each antibody binds its respective antigen to form a complex;

(b) a positive control comprising the 16 (±4) kDa *Sarcocystis neurona* antigen and a positive control comprising the 30 (±4) kDa *Sarcocystis neurona* antigen; and (c) a reagent for detecting the complex formed between the antibody and the *Sarcocystis neurona* antigen.

22. The kit of claim 21 wherein the reagent for detecting the complex consists of a labeled antibody against the antigen or antibody in the complex.

23. The kit of claim 22 wherein the label is selected from the group consisting of alkaline phosphatase, horseradish peroxidase, fluorescent compounds, luminescent compounds, colloidal gold, and magnetic particles.

24. The kit of claim 23 wherein the label is biotin which is reacted with peroxidase conjugate and then detected by reaction with an appropriate color forming substrate.

25. The kit of claim 24 wherein the biological sample is from the group consisting of serum, cerebrospinal fluid, and cell culture fluid from equine dermal cells infected with *Sarcocystis neurona* from a biological sample.

26. The kit of claim 21 wherein the monoclonal antibody against the antigen is immobilized on a support selected from the group consisting of a membrane or a plate.

27. The kit of claim 22 wherein the labeled antibody is a second monoclonal antibody.

28. A kit for the detection of disease caused by *Sarcocystis neurona* in an equine which comprises:

(a) a support with a monoclonal antibody against a first epitope of a 16 (±4) kDa *Sarcocystis neurona* antigen and a monoclonal antibody against a first epitope of a 30 (±4) kDa antigen immobilized on a surface of the support to bind the antigen in a biological sample from the equine;

(b) a first labeled monoclonal antibody against a second epitope of the 16 (±4) kDa antigen and a second labeled monoclonal antibody against a second epitope of the 30 (±4) kDa antigen to bind the antigen bound by the monoclonal antibody immobilized on the membrane; and (c) a reagent for detection of the first labeled monoclonal antibody bound to the 16 (±4) kDa antigen and a reagent for detection of the second labeled monoclonal antibody bound to the 30 (±4) kDa antigen.

29. The kit of claim 28 wherein the label is selected from the group consisting of alkaline phosphatase, horseradish peroxidase, fluorescent compounds, luminescent compounds, colloidal gold, and magnetic particles.

30. The kit of claim 29 wherein the label is biotin which is reacted with peroxidase conjugate and then detected by reaction with an appropriate color forming substrate.

31. The kit of claim 28 wherein the biological sample is selected from the group consisting of serum, cerebrospinal fluid, and cell culture fluid from equine dermal cells infected with *Sarcocystis neurona* from a biological sample.

32. The method of claim 28 wherein the monoclonal antibody against the antigen is immobilized on the support selected from the group consisting of a membrane or a plate.

33. A monoclonal antibody against a 16 (±4) kDa antigen of *Sarcocystis neurona*.

34. A monoclonal antibody against a 30 (±4) kDa antigen of *Sarcocystis neurona*.

35. An isolated DNA encoding a 16 (±4) kDa antigen of *Sarcocystis neurona*.

36. An isolated DNA encoding a 30 (±4) kDa antigen of *Sarcocystis* neurona.

* * * * *

UNITED STATES PATENT AND TRADEMARK OFFICE
CERTIFICATE OF CORRECTION

PATENT NO. : 6,344,337 B1
DATED : February 5, 2002
INVENTOR(S) : Linda S. Mansfield, Mary G. Rossano, Alice J. Murphy and Ruth A. Vrable It is certified that error appears in the above-identified patent and that said Letters Patent is hereby corrected as shown below:

Column 2,
Line 8, "*neuronaa*" should be -- *neurona* --.

Column 4,
Lines 32 and 33, "*neuronaa*" should be -- *neurona* --.
Line 34, "*neuronaa*" should be -- *neurona* --.

Column 5,
Line 14, "*neuronaa*" should be -- *neurona* --.
Lines 16 and 17, "*neuronaa*" should be -- *neurona* --.
Line 26, "*neuronaa*" should be -- *neurona* --.

Column 6,
Line 56, "*neuronaa*" should be -- *neurona* --.
Line 66, "*neuronaa*" should be -- *neurona* --.

Column 7,
Lines 5 and 7, "*neuronaa*" should be -- *neurona* --.
Lines 21 and 23, "*neuronaa*" should be -- *neurona* --.
Line 28, "*neuronaa*" should be -- *neurona* --.
Line 36, "*neuronaa*" should be -- *neurona* --.
Line 49, "*neuronaa*" should be -- *neurona* --.
Line 63, "*neuronaa*" should be -- *neurona* --.

Column 8,
Line 49, "*neuronaa*" should be -- *neurona* --.

Column 9,
Line 57, "*neuronaa*" should be -- *neurona* --.

Column 10,
Lines 14 and 16, "calorimetric" should be -- colorimetric --.

Column 11,
Line 23, "100 pg per" should be -- 100 Mg per --.

Column 12,
Line 18, "1for" should be -- for --.

UNITED STATES PATENT AND TRADEMARK OFFICE
CERTIFICATE OF CORRECTION

PATENT NO.     : 6,344,337 B1
DATED          : February 5, 2002
INVENTOR(S)    : Linda S. Mansfield, Mary G. Rossano, Alice J. Murphy and Ruth A. Vrable It is certified that error appears in the above-identified patent and that said Letters Patent is hereby corrected as shown below:

<u>Column 13,</u>
Line 18, "*neuronaa*" should be -- *neurona* --.
Line 50, "*neuronaa*" should be -- *neurona* --.

<u>Column 16,</u>
Line 18, "1.0 ∆g" should be -- 1.0 µg --.

<u>Column 17,</u>
Line 64, "*neuronaa*" should be -- *neurona* --.

<u>Column 18,</u>
Line 34, "µlate" should be -- plate --.
Line 35, "µlate" should be -- plate --.
Line 50, "(PNPP" should be -- (pNPP --.

<u>Column 19,</u>
Line 61, "µlus" should be -- plus --.

<u>Column 21,</u>
Line 58, "*neuronaa*" should be -- *neurona* --.

<u>Column 24,</u>
Line 11, "Aimonium" should be -- Ammonium --.

<u>Column 26,</u>
Line 66, "of Claim 24" should be -- of Claim 21 --.

Signed and Sealed this

Third Day of September, 2002

*Attest:*

*Attesting Officer*

JAMES E. ROGAN
*Director of the United States Patent and Trademark Office*